United States Patent [19]

Holtkamp

[11] Plant 4,415

[45] May 15, 1979

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "Optimara", Isselburg, Fed. Rep. of Germany

[21] Appl. No.: 880,123

[22] Filed: Feb. 22, 1978

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

An african violet known by the cultivar name North Carolina and having sturdy, upright flower stems, with 10–12 single red-purple flowers on each stem; non-dropping flowers, and vigorous and compact growth habit.

1 Drawing Figure

The present invention comprises a new and distinct cultivar of African Violet plant, botanically known as *Saintpaulia ionantha,* and hereinafter referred to by the cultivar name North Carolina. North Carolina referred to during the breeding and selection process by the numbers 17/9 and 69/77, is a product of a planned breeding program, and is principally characterized by its purple-red flowers which sit on strong, upright stems, and eight to ten flower stems, with each flower stem carrying up to 12 flowers.

The new cultivar was originated from a cross made in a controlled breeding program in Isselburg, Rhineland, Germany. The female, or seed parent is unpatented and identified as F III pink (color RHS 62-D). The male, or pollen parent, also unpatented, is identified as 4001 red (color RHS 71-A).

North Carolina was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of North Carolina, which in combination distinguish this African Violet as a new and distanct cultivar:

(1) Sturdy, upright flower stems.

(2) 10–12 single flowers, red-purple in flower color, on each flower stem.

(3) A fully blossomed plant has 8–10 flower stems.

(4) The flowers do not drop.

(5) Very compact growth habit, with excellent vigor.

The accompanying photographic drawing shows a typical specimen plant of the new cultivar. The colors appearing in the photograph are as true as possible with color illustrations of this type.

In the following description, flower color values are referenced to Horticultural Color Chart (Wilson), and the color values of foliage, buds, sepas, male and female parents, and reproductive organs are referenced to RHS Color Chart, 1966 edition. It is noted that it was difficult to obtain exact color values for the flowers, and the color values indicated below are as accurate as possible.

Botanical classification: *Saintpaulia ionantha,* Ramat. cv North Carolina.

Parentage:

*Male Parent.*—4001 red (RHS 71-A).

*Female Parent.*—F III pink (RHS 62-D).

Propagation: The new cultivar holds its distinguishing characteristics through successive propagations by leaf cuttings and by division of shoots.

Plant: From 6 cm. to 8 cm. tall when grown in pots, and approximately 23 cm. in diameter when fully grown.

*Leaves.*—General form: oblong. Diameter: 45–50 mm. Texture: soft and velvety. Veins: well pronounced. Color (upperside): 131-A. Color (underside): 187-A. Petiole: light reddish-brown.

*Flowers.*—Buds: ball-shaped, 6–7 mm. in diameter, color 72-B. Sepals: Spear-shaped, five in number. Color: 59A. Calyx: Attached to seed vessel and petals. Aspect: Funnel-shaped. Peduncle: 20–24 mm. long.

*Individual flowers.*—Size: 30–38 mm. in diameter. Color: Upperside: 732. Underside: Between 732/2 and 731/1. Borne: up to 12 flowers on each stem. Shape: Five flower petals, 2 small and 3 large. The three large petals are 20–22 mm. long and 14–15 mm. wide; the two small petals are 16–18 mm. long and 12–13 mm. wide. Arrangement: on erect and upright flower stems; each stem has up to 12 single flowers. Flowering time: 7–8 weeks after potting, the first flowers and buds appear; the plant is in full bloom after 8–10 weeks.

*Reproductive organs.*—Stamens: Two in number. Anthers: Four anthers, 7-B in color. Arrangement: The anthers are underneath the capsule with two short stems joined to the receptacle. Filaments: 4–5 mm. long. Styles: 7–8 mm. long, color 81-A. Pollen color: Color 7-C.

*Roots.*—Root system well developed; white when young and active, turning brownish when older.

*Disease resistance.*—Good, based on experience to date.

*General observations.*—North Carolina is a vigorously growing plant with very compact habit.

The flash of flowers out of the center of the plant is surrounded by dark green leaves, which are relatively small. Each flower stem carries at least 12 single blossoms.

I claim:

1. A new and distinct cultivar of african violet known by the cultivar name North Carolina and particularly characterized by the combined characteristics of sturdy, upright flower stems, with 10–12 single red-purple flowers on each stem; non-dropping flowers, and vigorous and compact growth habit.

* * * * *

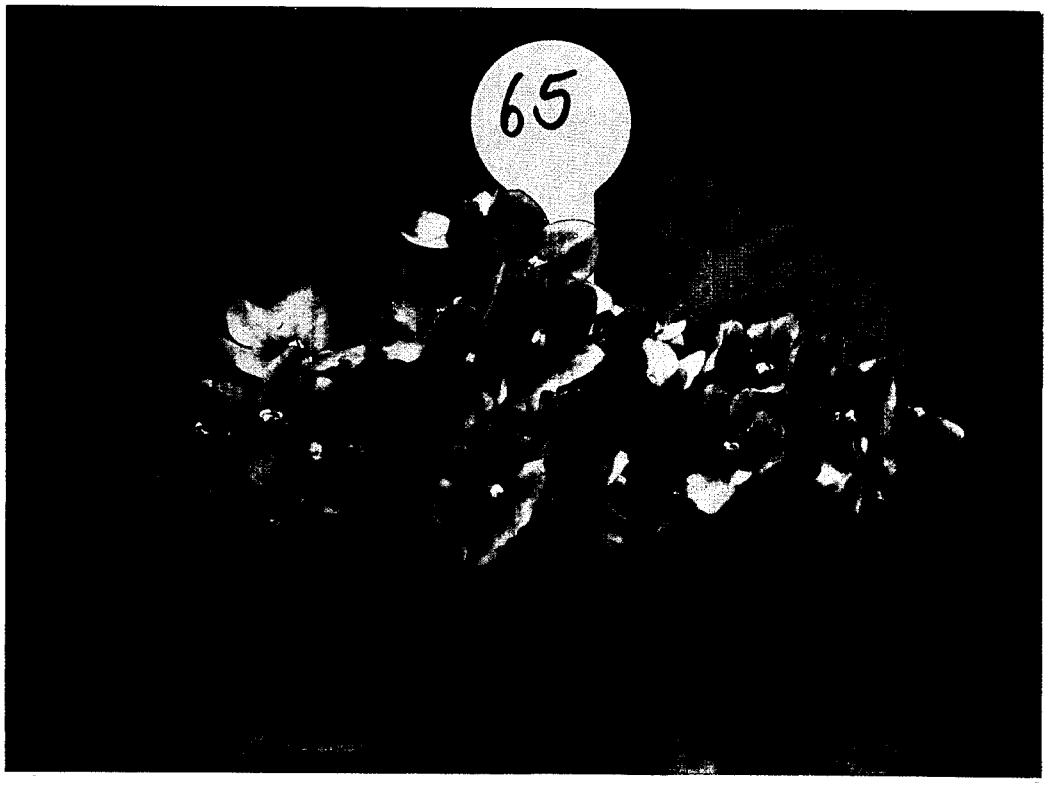
65